United States Patent
Spallek et al.

[11] Patent Number: 6,117,480
[45] Date of Patent: Sep. 12, 2000

[54] METHOD AND MEANS FOR COATING MEDICAL CANNULAS

[76] Inventors: Michael Spallek, Am Grauen Stein, 55218 Ingelheim; Jochen Heinz, Hauptstrasse 48, 55578 Vendersheim; Peter Kinast, Gartenstrasse 12, 71292 Friolzheim; Monika Löffler, Relenbergstrasse 27b, 70174 Stuttgart, all of Germany

[21] Appl. No.: 09/168,113

[22] Filed: Oct. 8, 1998

[30] Foreign Application Priority Data

Oct. 8, 1997 [DE] Germany ............ 197 44 367

[51] Int. Cl.⁷ .................. B05C 1/06; B05D 1/18; A61L 31/00
[52] U.S. Cl. .................. 427/2.3; 427/2.28; 427/429; 427/430.1; 427/355; 427/358; 427/371; 118/404
[58] Field of Search .................. 427/2.28, 2.3, 427/11, 429, 430.1, 155, 355, 356, 358, 369, 371; 118/404

[56] References Cited

U.S. PATENT DOCUMENTS

| | | | |
|---|---|---|---|
| 4,330,571 | 5/1982 | Stovall et al. | 427/120 |
| 4,624,817 | 11/1986 | Gusack et al. | 264/255 |
| 5,242,428 | 9/1993 | Palestrant | 604/265 |
| 5,266,359 | 11/1993 | Spielvogel | 427/388.4 |
| 5,676,990 | 10/1997 | Wawrzynski | 426/305 |
| 5,820,676 | 10/1998 | Bauerle | 118/421 |
| 5,863,614 | 1/1999 | Williamitis et al. | 427/429 |

FOREIGN PATENT DOCUMENTS

| | | |
|---|---|---|
| 0 491 547 A1 | 12/1991 | European Pat. Off. ........ A61L 29/00 |
| 0491547 | 6/1992 | European Pat. Off. . |
| 0494648 | 7/1992 | European Pat. Off. . |
| 0627474 | 12/1994 | European Pat. Off. . |
| 4124909 | 2/1992 | Germany . |

OTHER PUBLICATIONS

"Einstechkräfte medizinischer Kanülen in Labor und Praxis" by P. Kinast, Feinwerktechnik & Messtechnik, vol. 91 (1983), pp. 109 and 110.

Primary Examiner—Timothy Meeks
Assistant Examiner—Jennifer Kolb
Attorney, Agent, or Firm—Walter Ottesen

[57] ABSTRACT

Medical cannulas are typically provided with a silicone coating to improve incision performance. In order to produce a thin, continuous and even coating layer, silicone oil is provided at one side of an elastic foil and the foil is penetrated by the uncoated cannula from an opposite side. During this operation the cannula is wetted by the silicone oil. During withdrawal of the cannula from the foil, excess silicone oil is removed from the cannula and an even, particle-free thin coating which has no bulge- or bead-forming tendency during incision is obtained. Subsequently, the silicone coating is dried.

11 Claims, 3 Drawing Sheets

METHOD AND MEANS FOR COATING MEDICAL CANNULAS

FIELD OF THE INVENTION

The invention relates to a method of coating medical cannulas by siliconizing. The invention further relates to an apparatus for applying said method.

BACKGROUND OF THE INVENTION

Medical cannulas, also known as hollow needles, are used by inserting them into a vessel or into the skin to create access into the body of a living organism typically with hypodermic syringes in which case they are also called hypodermic needles, or with appropriate catheters. On the penetration side they are provided with a chamfer called the cut which has a specific cut-geometry. The customary cut-geometries are the facet cut for most clinical applications and the undercut which is preferably used for peripheral IV (intravenous) catheters.

The insertion of the cannula into the skin or into the vessels is predominantly felt to be painful by the patient and this has caused widespread anxiety and inherent aversion to the application of the syringe or the catheter. This pain and therefore the fear of the patient when faced with injections or with the fitting of catheters is ascribed mostly to the entering or penetration resistance of the cannula which thus ultimately determines what is known as the entrance quality.

The facts which determine penetration resistance, apart from the condition of the patient's skin, are:
cut-geometry and diameter of the cannula;
quality of finish;
sharpness and intact surface condition of the cannula tip and the cutting edge at the chamfer;
surface condition of the cannula; and,
surface treatment.

Damaged or blunt tips cause high resistance in the initial cutting stage, that is to say, in the process of first opening the skin or the vessel. The same applies to blunt cutting edges.

Cutting edges which are too short or blunt produce an incision of inadequate length entailing substantially more severe stretching of the tissues, potentially even tearing at the edges of the incision, but always generating a high circumferential tension and increased friction resistance during the positioning of the needle.

In order to reduce penetration resistance of a cannula it is known to provide the cannula with an anti-friction coating. The absence or inadequate application of surface coating causes greater friction resistance as a result of which the cannula is felt to be blunt by the patient.

It is currently customary to coat the cannula with so called "medical grade" silicone oil which is also listed in the relevant Standards (ISO 7864 (1993), ISO 7885-1 (1996), ISO 10555, ISO 11608, ISO 8537.2).

Most of these Standards contain the instruction that the coating should not be visible when regarded with normal eyesight and must not comprise any droplets or accumulations of silicone oil. ISO 7864 also specifies an upper limit for the permissible amount at 0.25 mg/cm2 of the lubricant relative to the cannula surface. This quantity of silicone must be regarded as the (absolute) upper limit. In view of the fact that during an injection silicone oil could enter into the body, and today free silicone is deemed to constitute a health hazard, it is important to keep the amount of free silicone oil in a cannula or syringe as low as possible.

Undiluted polydimethylsiloxane, having a viscosity of more than 1000 mm2/s and less than 30,000 mm2/s according to the national or European pharmacopoeia, is said to be a suitable and permitted lubricant. Having regard to the health risks of silicone products one endeavors to apply the smallest possible amounts of silicone oil which must however by sufficient to ensure the formation of a continuous layer on the cannula surface; and, good anti-friction properties.

Another possible way, besides minimizing the amount of silicone applied to the cannula, of keeping the quantity of silicone introduced into the body as low as possible resides in achieving improved adhesion of the silicone to the cannula surface. An example of this is coating with so called reactive silicone which, due to the polar groups, is intended to produce better bonding of the coating layer to the metal surface of the cannula and which by cross-linking produces a cohesive layer.

This type of coating is called "dry siliconization" since it has a rather dry (wax-like) appearance. This type of coating is widely used for large gauge cannulas and for surgical and acupuncture needles. With such dry siliconization only slightly better friction values can be attained at a disadvantage than with wet silicone coating processes. This is due, on the one hand, to the degree of cross-linking, that is to say to the mobility of the coating layer, and, on the other hand, to the thickness of the coating layer. Generally speaking, the pre-condition for lowest friction forces is the presence of a liquid lubricant which in the present case requires the presence of a "free" silicone oil. This is less present in the case of a dry siliconization. If, moreover, in a dry siliconization the layer thickness is too great then a viscous wax-like layer results and friction is slightly increased.

For application of the silicone coating to the cannula in principle all known technical coating methods are available:
dipping
spraying
printing
rolling
rubbing (with small sponges)
vapor deposition
high-vacuum precipitation.

However, since cannulas are inexpensive mass produced products it is common practice to use the more expensive siliconization methods only for special high-grade cannula types or packing means with needles or medical devices. The ordinary cannulas or needles are coated by simple methods and means which must be able to be integrated in an automatic assembly machine for mass production; for, as a rule, the cannula itself is initially not siliconized and only coated after assembly of the final product.

Basically there is a distinction applied between coating methods for what are generally called wet siliconizations and those for the aforementioned dry siliconizations.

For the application of wet silicone, the dipping method is widely used as it is simple and can be easily integrated in an automatic assembly process. It has the advantage that the cannula can easily be coated over its entire length simply by dipping or plunging the cannula completely into a silicone bath. Since the liquid level of the silicone container and the descent movement of the cannula can be comparatively easily measured and adjusted, the coating of a cannula over a defined length thereof is reliably adjustable.

Regarding the state of the art in dipping processes we refer, for example, to DE 41 24 909 A1 which describes a dipping method where the silicone solution is continuously fed in such a manner as to prevent thickenings, soiling and sedimentation or demixing. EP 0 494 648 A2 also describes a dipping process of this kind.

However, the silicone layers obtained by a dipping process are often too thick so that, contrary to regulations, they are visible and form droplets. It is particularly harmful that silicone particles may form which may arrive in the body of the patient. The principle "much gives much help" is not true in this case because thickly coated cannulas do not necessarily display the best friction characteristics. If no adequate bonding to the surface is formed the silicone will be displaced so strongly during incision that the friction values are comparatively high despite the thick coating and undesirable silicone bulges or beads tend to be formed.

In order to avoid such effects, it is frequently the practice to use diluted oils in the dipping process. Preferred diluents are halogenated hydrocarbons or alcohols or similar substances or also other organic solvents.

While coating layer quality can be improved by the better and more uniform cross-linking behavior, the solvents are to a considerable extent environmentally harmful as well as presenting risks of fire and explosion accidents. If water is used, on the other hand, a uniform emulsion must be assured which involves high technological expenses; moreover, the water must be removed from the needle surface after coating either by heat treatment or long storage periods.

A further inherent drawback of the dipping method resides in that silicone oil gets into the interior of the cannula and then inevitably also into the patient's body during the injection.

Coating by the methods of rubbing on, rolling on or printing which are equally suitable for automation will produce substantially thinner layers which may however be irregular so that some areas will have a thick coating (or droplet) whilst others are dry because the wetting of the cannula is very difficult to monitor automatically.

While spraying and vapor deposition will produce very even layers these processes take much longer and it is difficult to achieve an accurate setting for the coated surface area of the cannula. Moreover, the appropriate apparatus can be integrated in "clean space areas" only at considerable expense. Their use in final assembly machines and packing installations is therefore rather limited. A spray-coating or an ultrasonic atomizing process of this type was disclosed in EP 0627 474 A1.

The earlier mentioned so called dry silicone coatings are produced with cross-linked silicone oils. The cross-linking of the commonly used silicone oils with reactive fractions predominantly takes place at room temperature or raised temperature and normal air humidity. Alternatively, or additionally, ultraviolet radiation may also be applied. The duration of the cross-linking process will depend on the desired degree of cross-linking and on prevailing environmental conditions. It may be several hours in a thermocabinet or up to several days at room temperature. This means, however, that his kind of siliconization is practically not capable of application in an integrated continuous production on one machine unless the cannula remains exposed to the environment after the process, that is to say, in a container which is permeable by air and moisture, as is the case, for example, with acupuncture needles.

For this reason this type of siliconization is used only with partially, or semi-automatic processes and with pre-assembly machines, e.g. as a final operational step, so that the silicone layer can harden prior to final assembly. Here it is possible to take advantage of the benefits of the spray-coating method, namely the application of an even layer of which the thickness can be controlled by the holding time.

Dipping processes using these kinds of cross-linked silicone oils are, admittedly, also possible but there is a risk that the silicone may already partially cross-link in the dipping tank since there is a relatively large quantity of silicone oil in the tank, that is to say, a multiple of the layer to be applied, as a result of which silicone particles will be deposited on the needle surface.

EP 0 491 547 A1 describes silicone mixes suitable for use in different coating processes such as application by means of small sponges spraying rolling printing dipping and which require no lengthy cross-linking processes. This specification proposes for this purpose the use of so called polar non cross-linking polysiloxanes to which better adhesion to the cannula surface than that of a non cross-linking non-polar silicone coating is ascribed.

Tests have shown that it is not possible with the known methods to realize the relevant requirements according to the Standards, namely to apply a thinnest possible, continuous and even silicone layer to a cannula. In many cases the layer is either continuous and too thick, as occurs frequently with dipping processes, or flawed areas appear. This significantly impairs incision quality of the needle. Moreover, during insertion or placing of a needle cap, bulge or bead formation tends to occur in the silicone layer due to the presence of silicone particles.

SUMMARY OF THE INVENTION

The underlying aim and objective of this invention resides in conducting the initially defined process in a simple fashion in such a way as to enable a thin, uniformly continuous and particle-free silicone layer being applied to the cannula.

According to the invention this aim is achieved by adopting the following steps:

providing a supply of silicone oil at one side of an elastic foil which is preferably thin and highly elastic;

penetrating the foil on an opposite side to the silicone oil with an uncoated cannula;

wetting the cannula with the silicone oil;

withdrawing the wetted cannula from the foil whilst removing excess oil from the cannula; and drying the silicone coat.

The method according to the invention is very easy to apply and, surprisingly, due to the stripping effect of the foil during withdrawal of the wetted cannula, it enables an invisible thin, continuous and even silicone layer to be obtained. Cannulas which have been coated in accordance with the method of this invention therefore have a very high incision performance, do not tend towards bead formation during their insertion and have a particle-free surface.

Surprisingly, it was found that during withdrawal of the cannula, the coating is not so stripped off as to entail any deterioration in anti-friction behavior. Rather, the result is an evening out of the layer and removal of surplus amounts of silicone and, above all, removal of any potentially adhering particles which are held back on the rear side of the foil. This, on the one hand, allows the use of undiluted silicone oils thereby avoiding the above described disadvantages. Furthermore, it is now possible to avoid the process-related drawbacks of particle formation in the dipping method and, above all, in the spongelet application method (wetting by means of a sponge saturated with silicone oil) due to abrasion.

A further potential advantage arises from the fact that in view of the positive silicone oil removal as compared with draining after dip-coating, the coating process time can be shortened which yields improved productivity.

According to a further development of this invention the foil is a synthetics material as typically used for the pre-scribed 100%-in-line penetration test of finished cannulas. Such a material is preferably polyurethane (PU), typically with a thickness of 0.35 mm.

This ensures that the cannula tip is not damaged when passing through the foil inasmuch as the test material was chosen precisely from this point of view.

As regards the provision of silicone oil at one side of the foil, various possibilities are conceivable according to embodiments and further developments of the invention.

According to a first embodiment of the invention the process is so conducted that with a horizontally extending foil the silicone oil is provided in a dipping bath arranged beneath the foil and the perforation of the foil by the uncoated cannula dipping into the bath occurs from above.

Due to the described stripping effect during withdrawal of the cannula (which has been wetted in the dipping bath) from the foil, the earlier described disadvantages appertaining to conventional dip-coating processes are avoided.

In order to avoid penetration of the silicone oil into the interior of the cannula, the inside of the cannula may be additionally subjected to excess pressure (air or other gases).

According to a second embodiment of the invention, the process is so conducted that with a horizontally extending foil the silicone oil is provided by two silicone oil-soaked spongelets mounted for horizontal movement beneath the foil and penetration of the foil by the uncoated cannula occurs from above, the spongelets being moved apart during foil penetration by the uncoated cannula and then being moved together for wetting the descended cannula with silicone oil. This spongelet method enables a particularly even coating layer to be formed.

A special advantage of the spongelet applicator method resides in that, different to dipping, spraying and another method of wetting the cannula by means of a silicone-oil drip which will be described below, no silicone oil can get into the interior of the cannula, the lumen. Furthermore, undiluted silicone oils can be used and potential abrasive detritus of the spongelet is reliably held back.

It is also conceivable to conduct the process in such a manner that the silicone oil is applied in the form of drops on top of a horizontally extending foil and the latter is perforated from below by the cannula. Alternatively to the application of drops to the topside of the foils a silicone-oil coating layer may be provided on the foil. However, these two alternative modes of holding the silicone oil ready for siliconization of the cannula have a limited range of application.

According to a further development of the invention the friction data involved by the withdrawal of the wetted cannula from the foil are measured. Since these friction data depend crucially on the siliconization result of the cannula shank it is thus possible with great advantage in a very simple way to obtain a 100%-in-line test of the coating result. Moreover, during the downward movement of the cannula, the integrity of the cannula tip can be easily checked by measuring the penetration force of the foil. In this way, a 100%-in-line check of the cannula tip is also made.

BRIEF DESCRIPTION OF THE DRAWINGS

Further details and aspects of the invention arise from the following specific description of examples of embodiments illustrated in the drawings wherein.

DESCRIPTION OF THE PREFERRED EMBODIMENTS OF THE INVENTION

Figure 1:
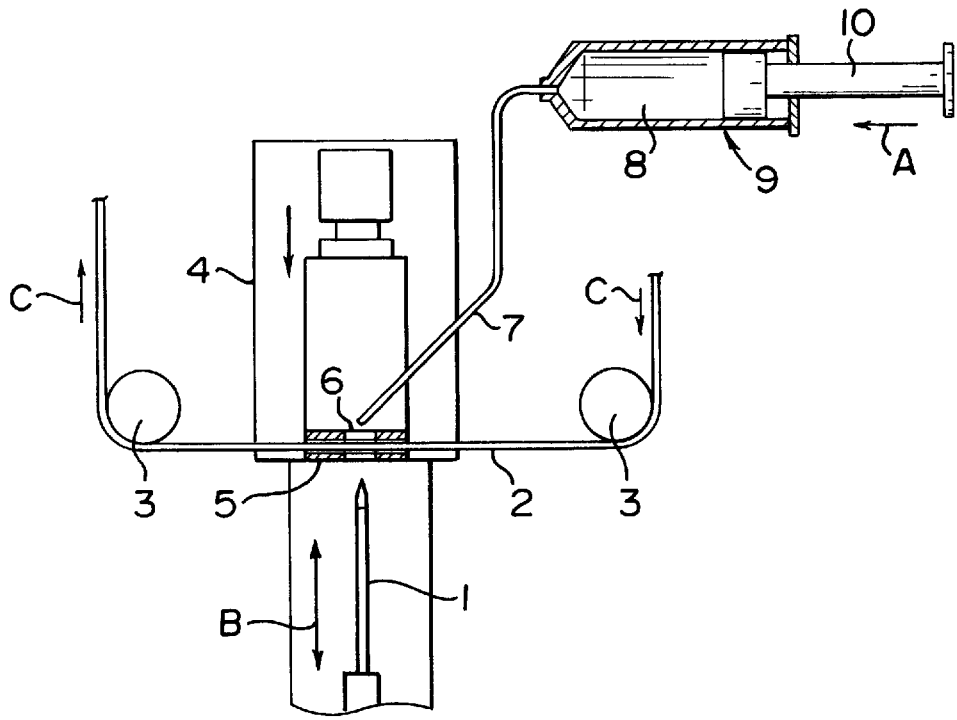
FIG. 1 is a diagrammatic representation of one embodiment of the foil method according to this invention, wherein the silicone oil is provided in the form of drops on the foil.

FIG. 1 shows in schematic representation one possible embodiment of the method according to the invention and associated apparatus. 1 is a cannula in the form of a hypodermic needle which by siliconization is to be provided with an anti-friction coating in order to reduce penetration force.

A thin highly elastic foil 2 is horizontally guided under tension in rails 5 via guide pulleys 3 in a coating station 4. Arrows C indicate the direction of movement of the elastic foil 2. The rails 5 comprise a central hole 6 into the region of which projects the output line 7 of a dosing device 9 filled with silicone oil 8. When the plunger 10 of this dosing device is moved in the direction of the arrow A, a silicone drop is discharged from the outlet opening of line 7 and travels through the central hole 6 to the foil 2. Thereafter the foil 2 with the silicone drop is perforated from that side thereof which is opposite the drop i.e. from below. On being thus penetrated, the silicone drop will conically wrap around the cannula 1. Thereafter, as indicated by the arrow B, the cannula 1 is withdrawn from the silicone drop and the foil 2 during which phase the cannula 1 passes once more through the silicone drop but when it passes again through the foil 2 all excess of silicone is held back and stripped off. Subsequently the remaining silicone coat is dried off in the usual way.

It will be understood that FIG. 1 merely illustrates the principle of the apparatus used to carry out the method according to the invention. Likewise the dosing device 9 is only symbolically represented in the form of a piston/cylinder dosing unit. It is certainly also possible to make use of other types of dosing devices. The man of the art also has at his disposal other constructional arrangements suitable for guiding the foil 2 and displacing the cannula 1.

Figure 2:
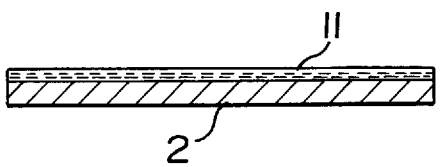
FIG. 2 is a detail sketch showing the provision of the silicone oil in the form of a silicone coating layer applied to the foil.

Instead of a silicone oil drop being applied to the foil it is also possible, as shown in detail on a larger scale in FIG. 2, for the silicone oil to be provided in a silicone oil layer 11 applied to the topside of the foil 2.

Figure 3:
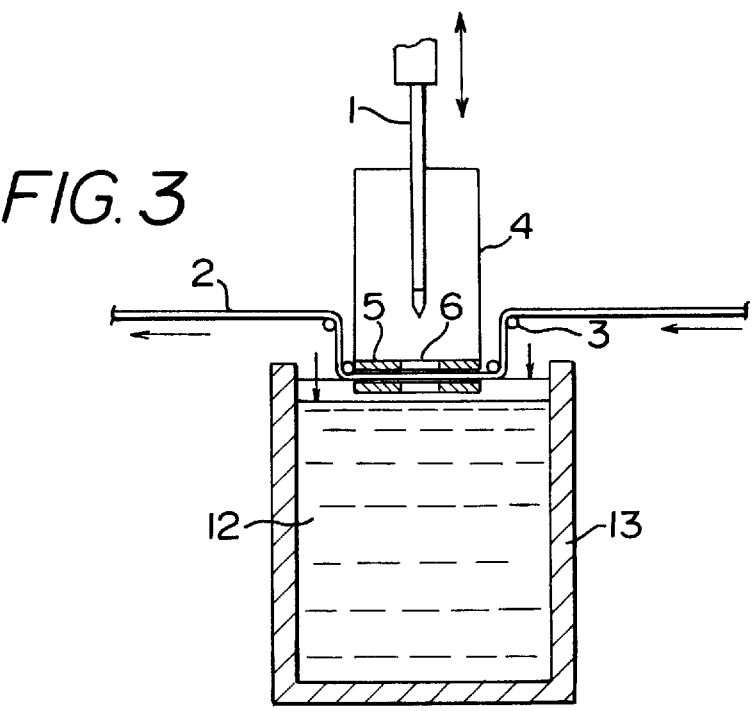
FIG. 3 is a diagrammatic illustration of an embodiment of the foil method according to the invention with the silicone oil contained in a dipping bath.

FIG. 3 shows a further embodiment of the invention, like parts carrying the same references as in FIG. 1. In the embodiment according to FIG. 3, the cannula 1 which is to be siliconized is arranged above the foil 2 in the coating station 4. Beneath the foil 2 there is a dipping bath in the form of a container 13 filled with silicone oil 12. For the purpose of being coated, the cannula 1 is displaced downwards through the central hole 6 and penetrating foil 2 into the dipping bath 12, 13. Then the cannula is pulled up again and as it is extracted from foil 2, all excess silicone oil is stripped off so that the earlier described disadvantages appertaining to conventional dipping methods are obviated.

Figure 4:
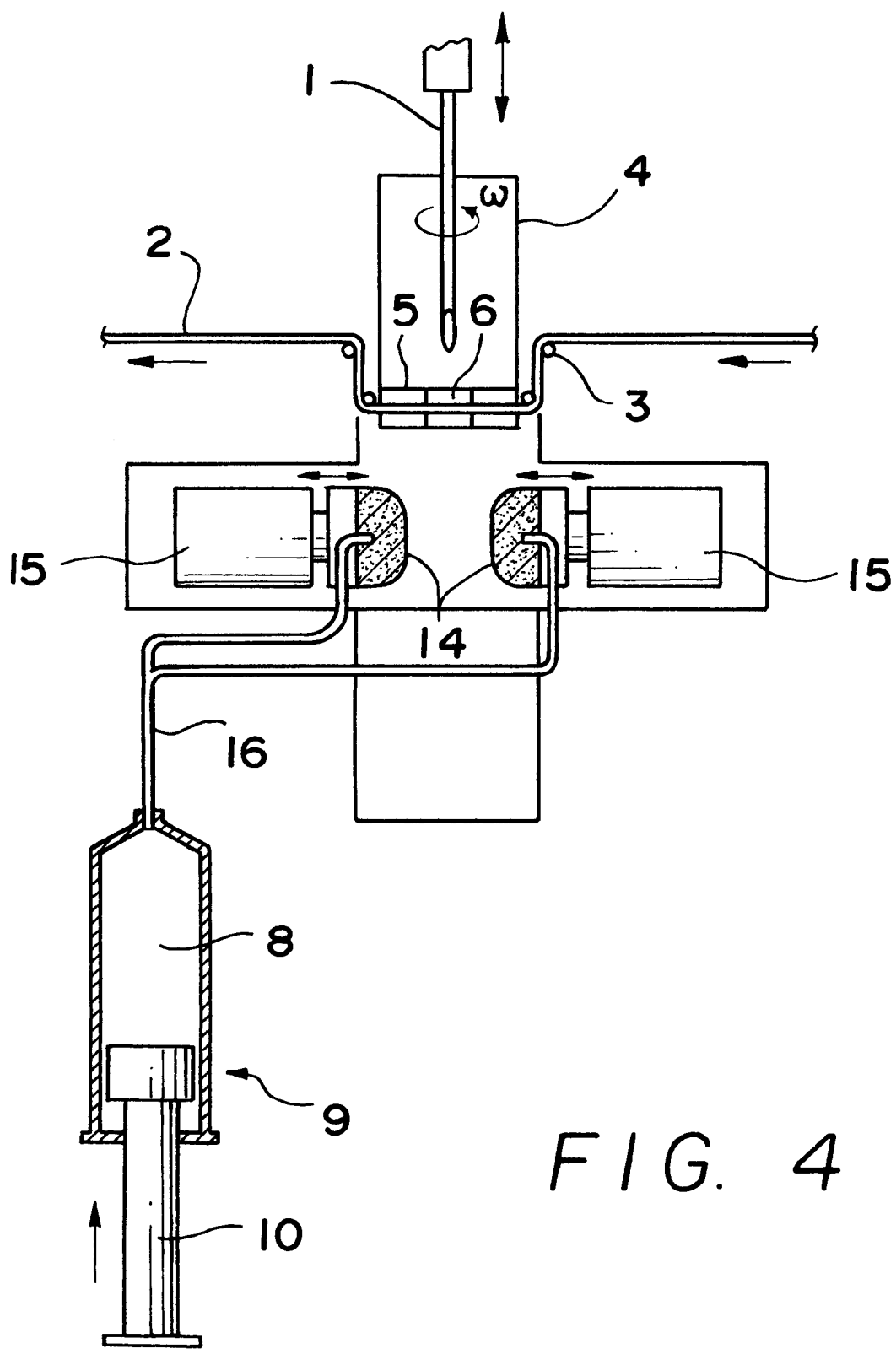
FIG. 4 is a diagrammatic illustration of a further embodiment of the foil method according to the invention with the silicone oil being provided by means of spongelets.

FIG. 4 shows a further, preferred embodiment of the invention, like parts being again indicated by like references to FIGS. 1 and 3. In the arrangement according to FIG. 4 two spongelets 14 which are adapted to be horizontally displaced by sliding units 15 are provided beneath the foil 2 in the coating station 4. The spongelets 14 are impregnated, preferably in a volume-controlled manner, with silicone oil 8 by means of dosing unit 19.

During penetration of the foil 2 by the rotating or stationary cannula 1, the spongelets 14 are relatively spaced apart as shown. After penetration of the foil they are driven up to the still rotating or stationary cannula and wet the cannula shank. Then the cannula is driven upwards again, any excess silicone oil or potentially adhering sponge particles being stripped off as the cannula is pulled out of the foil 2.

The special advantage of the sponge applicator method resides in that, in contrast to what occurs with dipping, spraying and the other described foil methods, no silicone oil can get into the interior, i.e. the lumen, of the cannula. Moreover, it is now possible to use undiluted silicone oils.

It was found that with the aid of the foil method according to the invention a particle-like thin, continuous and even silicone layer can be applied to the surface of the cannula 1 which repeatedly furnished the same coating results and could therefore also be automated. In the case of the embodiment according to FIG. 4 moreover, the lumen of the cannula remains clear of silicone oil which is a great advantage.

Figure 5:
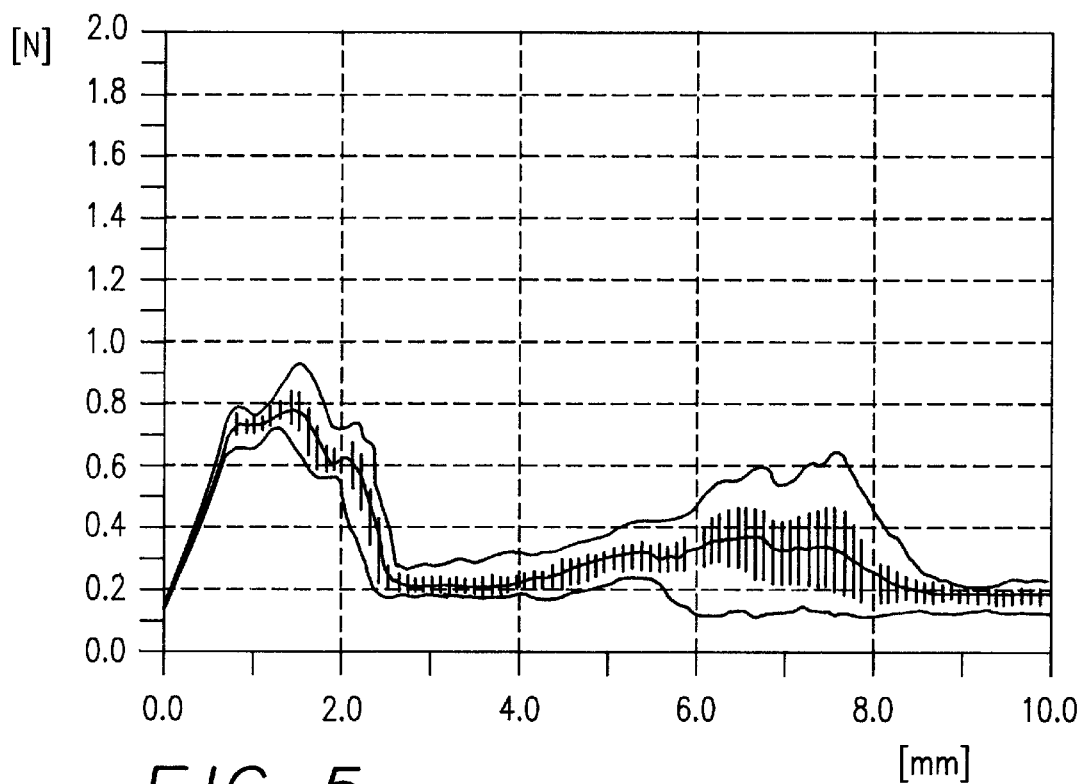
FIG. 5 is a force-distance diagram describing the incision force and the friction force of a commercially typical cannula; and, FIG. 6 is a diagram corresponding to FIG. 5 for a cannula which has been coated by the foil method according to this invention.
Figure 6:
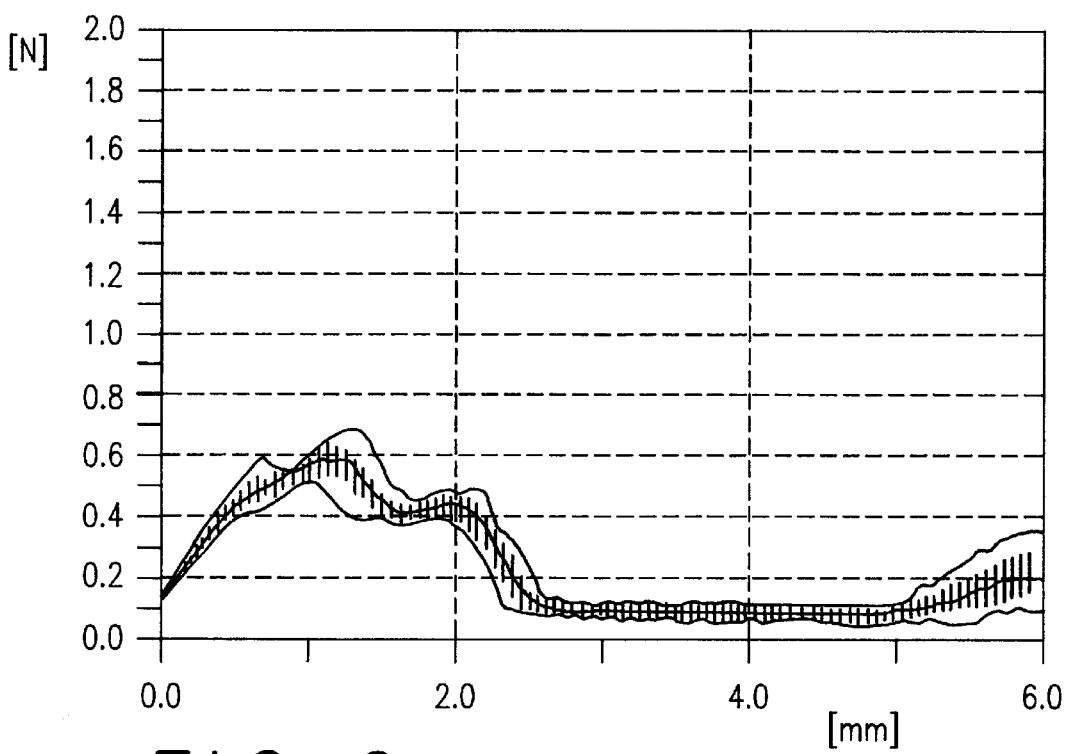

The advantages of the method according to this invention are clearly revealed by a comparison of the force-distance diagrams according to FIGS. 5 and 6. These graphs can be plotted with a conventional incision-measuring kit of the kind described for example in the article by P. Kinast entitled "Incision forces of medical cannulas in laboratory and practice" published in "Feinwerktechnik & Messtechnik" 91 (1983) 3 pages 109–110.

The measured values plotted in the graphs are based on the vertical penetration of a PU foil, 0.35 mm thickness, at a speed of 100 mm/min. In FIG. 5 measured distance is 10 mm in FIG. 6 it is 6 mm.

In the case of conventional commercially available cannulas with the graph according to FIG. 5 the following data are shown:

| maximum force: | Fmax = 0.82 N |
| --- | --- |
|  | Ffrict. = 0.27 N |

In the case of a cannula which was siliconized in accordance with the invention corresponding to the diagram FIG. 6, the corresponding data are as follows:

| maximum force: | Fmax = 0.62 N |
| --- | --- |
|  | Ffrict. = 0.09 N |

This reveals the largely uniform friction force with the cannula coated by the method according to the invention with the lower maximum incision force and the lower shank friction.

Microscopic tests have confirmed this effect. In tests applied to conventional commercial cannulas it was found that droplets or accumulations of silicones or dry spots were present, that is to say, no uniformly even layer of coating had been produced on the cannula which significantly detracted from incision performance quality.

By contrast, with cannulas which had been siliconized by the method according to this invention a thin, continuously extending uniformly even and particle-free layer was found which has no tendency to bulge or bead formation during the placing of a cannula cap or during an injection.

The foils 2 preferably consist of a material of the kind which is typically used for a regulation 100%-in-line penetration test of manufactured cannulas. Such a material is preferably polyurethane (PU) with a thickness grade of approximately 0.35 mm. The use of this material, which is also demanded by French Standard AFNOR NFS 90 040 for penetration testing makes sure that the cannula 1 is in no way altered during its incision into the foil.

The silicone oil may consist of the following silicone compounds:

non cross-linked polar silicones or polysiloxanes, in particular non-reactive polydimethyldisiloxanes (PDMS) or reactive polymericsiloxanes, copolymers of alkylamine-modified methoxysiloxanes with an aminoalkyl group.

The foil method according to the invention also enables in a simple manner a 100%-in-line testing of the coating result by measuring during the extraction of the wetted cannula 1 from the foil 2 the friction data generated thereby which sensibly depend on the siliconization result.

The cannula which has been coated according to the present invention may be used in a variety of ways, e.g. as a hypodermic needle for syringes, as an attachment to tissue-sample-taking devices, in association with catheters etc. For preference it is used as an integrated hypodermic needle in ready-manufactured syringes made of glass or plastic.

It is understood that the foregoing description is that of the preferred embodiments of the invention and that various changes and modifications may be made thereto without departing from the spirit and scope of the invention as defined in the appended claims.

What is claimed is:

1. A method of coating a medical cannula by siliconization comprising the steps of:

moving an elastic foil so that an unperforated segment thereof is at a coating location;

providing silicone oil at one side of said elastic foil;

simultaneously perforating and penetrating said elastic foil from the other side thereof at said segment with an uncoated cannula to reach said silicone oil;

wetting the cannula with the silicone oil on said one side of said elastic foil;

withdrawing the wetted cannula from said elastic foil while removing excess silicone oil from the cannula as the cannula again passes through said elastic foil; and, drying the silicone coating.

2. The method of claim 1, wherein the foil is a synthetic material which is used for a regulation 100%-in-line penetration test of manufactured cannulas.

3. The method of claim 1, wherein the synthetic material is polyurethane (PU).

4. The method of claim 1, wherein the foil thickness is 0.35 mm.

5. The method of claim 1, wherein the silicone oil is a polar non cross-linking polysiloxane.

6. The method of claim 1, wherein, with said elastic foil extending horizontally, the silicone oil is provided in a dipping tank arranged beneath the foil and the penetration of the foil by the uncoated cannula dipping into the tank occurs from above.

7. The method of claim 1, wherein, with said elastic foil extending horizontally, the silicone oil is provided by two sponges impregnated with silicone oil and mounted for horizontal movement beneath the foil and penetration of the foil by the uncoated cannula occurs from above, the sponges being mutually moved apart during foil penetration by the uncoated cannula and being mutually moved together for wetting the descended cannula with silicone oil after penetration of the foil.

8. The method of claim 1, wherein, with said elastic foil extending horizontally, the silicone oil is provided by at least one drop of silicone oil applied to the topside of the foil and that penetration of the foil by the uncoated cannula occurs from beneath.

9. The method of claim 1, wherein, with said elastic foil extending horizontally, the silicone oil is provided by means of a silicone oil layer applied to the top side of the foil and foil penetration by the uncoated cannula occurs from below.

10. The method of claim 1, wherein, during the withdrawal of the wetted cannula from the foil, the friction data thereby produced are measured as a measure of the siliconization result.

11. The method of claim 1, wherein said segment of said elastic foil is guided under tension to said coating location utilizing guide rollers.

* * * * *